US012295847B2

(12) United States Patent
Neustadter

(10) Patent No.: US 12,295,847 B2
(45) Date of Patent: *May 13, 2025

(54) IMPLANTABLE VENTRICULAR BAND FOR IMPROVING CARDIAC FUNCTION

(71) Applicant: Cardiac Success Ltd., Yokneam (IL)

(72) Inventor: David Neustadter, Nof Ayalon (IL)

(73) Assignee: CARDIAC SUCCESS LTD., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/241,670

(22) Filed: Sep. 1, 2023

(65) Prior Publication Data
US 2023/0404759 A1 Dec. 21, 2023

Related U.S. Application Data

(63) Continuation of application No. 18/089,497, filed on Dec. 27, 2022, which is a continuation of application No. 17/711,567, filed on Apr. 1, 2022, now Pat. No. 11,564,798, which is a continuation of application No. 16/695,645, filed on Nov. 26, 2019, now Pat. No. 11,318,018, which is a continuation-in-part of application No. 16/689,151, filed on Nov. 20, 2019,
(Continued)

(51) Int. Cl.
*A61F 2/24* (2006.01)
*A61M 25/09* (2006.01)
*A61M 25/10* (2013.01)

(52) U.S. Cl.
CPC .......... *A61F 2/2487* (2013.01); *A61F 2/2457* (2013.01); *A61F 2/2466* (2013.01); *A61M 25/09* (2013.01); *A61M 25/10* (2013.01); *A61F 2220/0075* (2013.01); *A61M 2205/0272* (2013.01)

(58) Field of Classification Search
None
See application file for complete search history.

(56) References Cited

U.S. PATENT DOCUMENTS 6,629,534 B1 10/2003 St. Goar et al.
7,331,972 B1 2/2008 Cox
(Continued)

FOREIGN PATENT DOCUMENTS

CN 102869321 A 1/2013
EP 2922501 A 9/2015
(Continued)

OTHER PUBLICATIONS

Office Action issued in corresponding Chinese Application No. 201880033678.6, dated May 7, 2021 (20 pages).
(Continued)

*Primary Examiner* — Kennedy Schaetzle
(74) *Attorney, Agent, or Firm* — FINNEGAN, HENDERSON, FARABOW, GARRETT & DUNNER LLP

(57) ABSTRACT

The present disclosure provides methods of improving cardiac function, including delivering a band to a ventricle of a heart via at least one catheter; guiding the band through the heart to form a loop; pulling walls of the ventricle of the heart inwards by tightening the band following formation of the loop; following tightening, locking the band in the loop; and removing the at least one catheter from the heart.

20 Claims, 8 Drawing Sheets

Related U.S. Application Data now Pat. No. 11,344,417, which is a continuation of application No. 16/355,971, filed on Mar. 18, 2019, now Pat. No. 10,517,729, which is a continuation of application No. 16/027,839, filed on Jul. 5, 2018, now Pat. No. 10,271,950, which is a continuation of application No. 15/938,241, filed on Mar. 28, 2018, now Pat. No. 10,058,428.

(60) Provisional application No. 62/477,461, filed on Mar. 28, 2017.

(56) References Cited

U.S. PATENT DOCUMENTS

| | | | |
|---|---|---|---|
| 9,125,632 B2 | 9/2015 | Loulmet et al. | |
| 9,125,742 B2 | 9/2015 | Yoganathan et al. | |
| 9,867,702 B2 | 1/2018 | Keränen | |
| 9,877,833 B1 | 1/2018 | Bishop | |
| 9,937,044 B2 | 4/2018 | Sutherland | |
| 10,010,419 B2 | 7/2018 | Yoganathan et al. | |
| 10,058,428 B1 | 8/2018 | Neustadter | |
| 10,271,950 B2 | 4/2019 | Neustadter | |
| 10,517,729 B2 | 12/2019 | Neustadter | |
| 10,743,991 B2 * | 8/2020 | Brown | A61F 2/2457 |
| 2005/0197696 A1 | 9/2005 | Duran | |
| 2006/0229708 A1 | 10/2006 | Powell | |
| 2007/0100439 A1 | 5/2007 | Cangialosi et al. | |
| 2007/0255396 A1 | 11/2007 | Douk et al. | |
| 2009/0082619 A1 | 3/2009 | De Marchena | |
| 2009/0099410 A1 | 4/2009 | De Marchena | |
| 2009/0234318 A1 | 9/2009 | Loulmet | |
| 2010/0121437 A1 | 5/2010 | Subramanian | |
| 2010/0185278 A1 | 7/2010 | Schankereli | |
| 2010/0210899 A1 | 8/2010 | Schankereli | |
| 2010/0298929 A1 * | 11/2010 | Thornton | A61F 2/246 |
| | | | 623/2.1 |
| 2011/0015476 A1 | 1/2011 | Franco | |
| 2011/0060407 A1 | 3/2011 | Ketai | |
| 2014/0379006 A1 | 12/2014 | Sutherland | |
| 2017/0119368 A1 | 5/2017 | Solem | |
| 2017/0135818 A1 | 5/2017 | Axelrod | |
| 2017/0156861 A1 | 6/2017 | Longoria | |
| 2017/0181851 A1 | 6/2017 | Annest | |
| 2018/0296340 A1 | 10/2018 | Yoganathan et al. | |
| 2019/0151093 A1 | 5/2019 | Keidar et al. | |
| 2019/0358037 A1 | 11/2019 | McAfee et al. | |
| 2019/0365539 A1 | 12/2019 | Rabito et al. | |
| 2019/0380699 A1 | 12/2019 | Bak-Boychuk et al. | |
| 2020/0107932 A1 | 4/2020 | Rabito et al. | |
| 2021/0161667 A1 | 6/2021 | Hou et al. | |

FOREIGN PATENT DOCUMENTS

| | | |
|---|---|---|
| WO | WO 2004/112651 A2 | 12/2004 |
| WO | WO 2009/155561 A2 | 12/2009 |
| WO | WO 2014/080338 A1 | 5/2014 |
| WO | WO-2016/180677 A1 | 11/2016 |
| WO | WO-2020-227556 A1 | 11/2020 |

OTHER PUBLICATIONS

Office Action in Chinese Application No. 201880033678.6, dated Jan. 5, 2022 (27 pages).

Office Action in Australian Application No. 2018247166, dated Mar. 7, 2022 (7 pages).

* cited by examiner

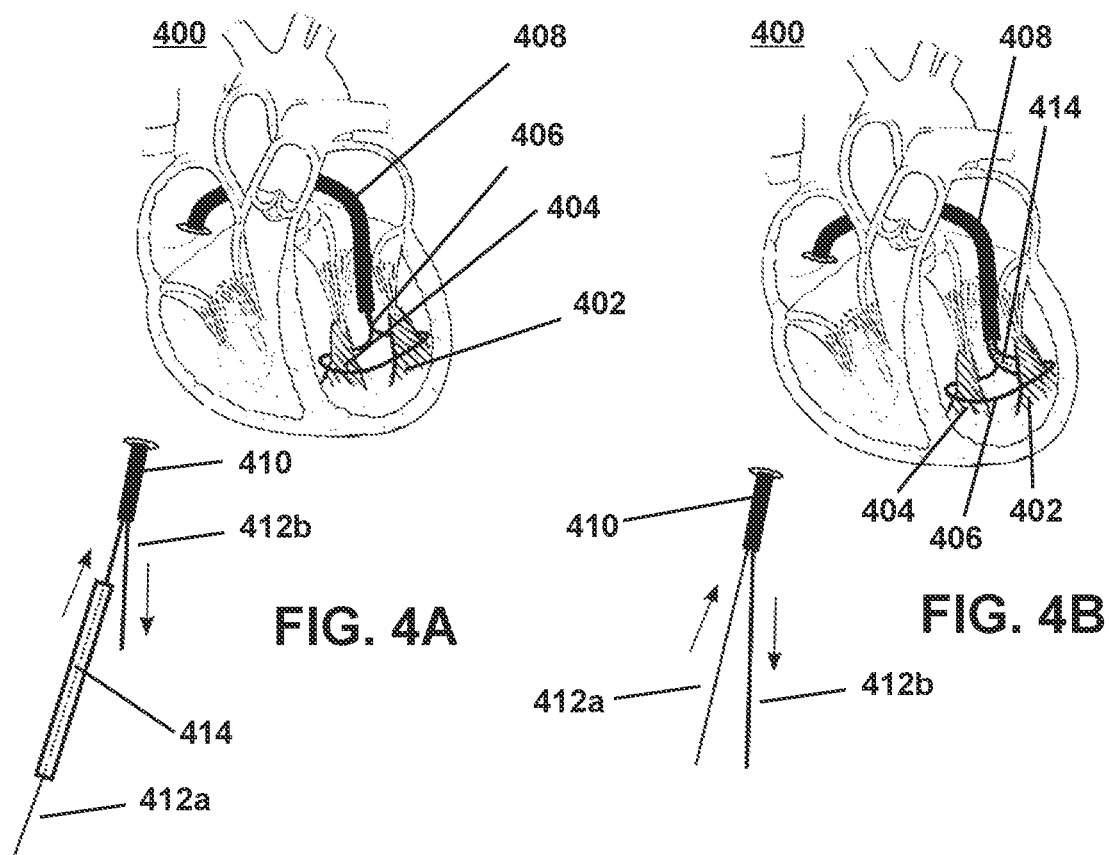
FIG. 4A
FIG. 4B
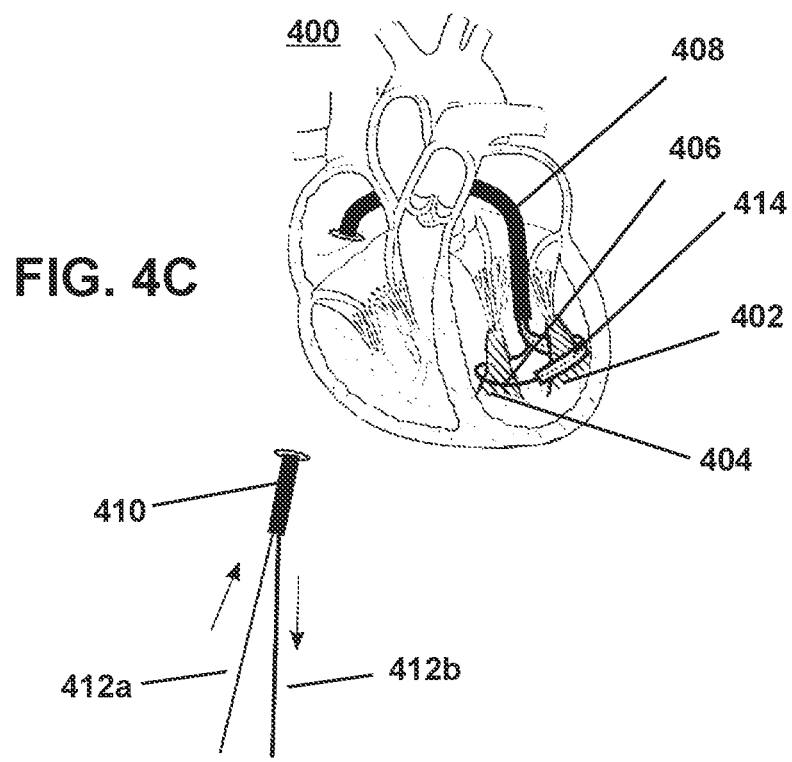
FIG. 4C

IMPLANTABLE VENTRICULAR BAND FOR IMPROVING CARDIAC FUNCTION

CROSS-REFERENCE TO RELATED APPLICATIONS

This application is a continuation of U.S. patent application Ser. No. 18/089,497, filed Dec. 27, 2023, which is a continuation of U.S. patent application Ser. No. 17/711,567, filed Apr. 1, 2022, (now U.S. Pat. No. 11,564,798), which is a continuation of U.S. patent application Ser. No. 16/695,645, filed Nov. 26, 2019 (now U.S. Pat. No. 11,318,018), which is a continuation-in-part of U.S. patent application Ser. No. 16/689,151, filed Nov. 20, 2019 (now U.S. Pat. No. 11,344,417), which is a continuation of U.S. patent application Ser. No. 16/355,971, filed Mar. 18, 2019 (now U.S. Pat. No. 10,517,729), which is a continuation of U.S. patent application Ser. No. 16/027,839 (now U.S. U.S. Pat. No. 10,271,950), filed Jul. 5, 2018, which is a continuation of U.S. patent application Ser. No. 15/938,241 (now U.S. Pat. No. 10,058,428), filed Mar. 28, 2018, which claims the benefit of U.S. Provisional Application No. 62/477,461, filed Mar. 28, 2017. The disclosures of the above-identified applications are expressly incorporated herein by reference in their entireties.

FIELD OF THE INVENTION

Some applications of the present invention relate in general to devices and methods of improving cardiac function. More specifically, some applications of the present invention relate to devices and methods of delivering a band to encircle a plurality of papillary muscles in a heart of a body.

BACKGROUND

There is significant evidence in the medical literature that repositioning the papillary muscles within the ventricles of the heart during atrioventrical valve repair surgery improves outcomes. The displacement of the papillary muscles, due to ischemia, heart failure, or other causes of ventricular reshaping, results in tethering of the valve leaflets which interferes with their normal functioning. Repairs that focus only on the valve annulus often result in recurrence of regurgitation due to leaflet tethering.

There is also significant evidence in the medical literature that ventriculoplasty, repairing the distorted geometry of the ventricle to approximate the geometry of a healthy ventricle, results in a significant improvement in ventricular function.

Numerous methods of papillary muscle repositioning and ventriculoplasty are described in the medical and patent literature. However, these methods of papillary muscle repositioning and ventriculoplasty are typically performed during an open heart surgery. Therefore, there is a need for a less invasive device and method of performing papillary muscle repositioning and/or ventriculoplasty. In particular, there is a need for a device and method of performing papillary muscle repositioning and/or ventriculoplasty via a catheter. Moreover, although the literature suggests papillary muscle repositioning and ventriculoplasty, suggested devices and methods have had little commercial success. There is therefore a need for improved devices and methods, regardless of whether delivered via a catheter or in some other way.

SUMMARY OF A FEW ASPECTS OF THE DISCLOSURE

The embodiments of the present disclosure include devices and methods of improving cardiac function. Advantageously, the exemplary embodiments provide a method of improving cardiac function by delivering at least one guidewire to a ventricle of the heart in order to encircle a band through the spaces among the trabeculae of the ventricular wall and/or around a plurality of papillary muscles. Various embodiments of the disclosure may include one or more of the following aspects.

In accordance with an embodiment of the present disclosure, a method of improving cardiac function is provided, the method comprising transcutaneously inserting at least one catheter into a heart, delivering a band to a ventricle of the heart via the at least one catheter, guiding the band through a plurality of spaces among the trabeculae in the ventricle of the heart, tightening the band in a single loop, locking the band in a loop, and removing the at least one catheter from the heart.

In some embodiments, the method of improving cardiac function may further comprise pulling a plurality of papillary muscles in the ventricle toward each other by tightening the band in the single loop. In some embodiments, the plurality of spaces among the trabeculae are located along walls of the ventricle of the heart. Accordingly, the method of improving cardiac function may comprise pulling the walls of the ventricle of the heart inwards by tightening the band in the single loop and locking the band in the loop. In accordance with some embodiments of the present disclosure, the method of improving cardiac function may further comprise locking the band around the trabeculae after tightening the band such that the band may pull the walls of the ventricle inwards.

In other embodiments of the present disclosure, the at least one catheter may be pre-shaped to pass through the plurality of spaces among the trabeculae, to thereby aid in guiding the band through the plurality of spaces among the trabeculae. In some embodiments, locking the band in the loop may include passing a pull-string through the band, pulling at least one end of the pull-string through the at least one catheter to tighten the band, and locking the pull-string into the loop. In some embodiments, the pull-string may be a self-locking pull-string. In other embodiment, the pull-string may be locked into the loop via a transcatheter suture lock, or any other locking mechanism capable of locking the pull-string into a loop. In some embodiments, tightening the band in the single loop may include tightening the band until the loop reaches a predefined circumference.

In another embodiment of the present disclosure, the band may include a hollow tube. In other embodiments, at least a portion of the band may include a hollow tube, whereas another portion of the band may not include a hollow tube. In some embodiments of the present disclosure, the band may include at least one of polytetrafluoroethylene (PTFE), expanded polytetrafluoroethylene (ePTFE), and/or Dacron.

According to another embodiment of the present disclosure, a method of improving cardiac function is provided, the method comprising transcatheterly delivering at least one guidewire to a ventricle of a heart, looping the at least one guidewire through a plurality of spaces among a trabeculae in the ventricle of the heart, directing, using the at least one guidewire, a band through the plurality of spaces among the trabeculae, tightening the band in a single loop, and transcatheterly removing the at least one guidewire from the heart.

According to an embodiment of the present disclosure, directing the band may include guiding the band through a plurality of spaces among trabeculae between the papillary muscles and a wall of the ventricle of the heart. In some embodiments, the plurality of spaces among trabeculae may be along the walls of the ventricle. In some embodiments, directing the band using the at least one guidewire may include connecting an end of the band to a distal end of the guidewire, and pulling a proximal end of the guidewire while the guidewire is looped around the plurality of spaces among the trabeculae, thereby pulling the band through the plurality of spaces among the trabeculae.

In some embodiments, the method of improving cardiac function may further comprise pulling a plurality of papillary muscles in the ventricle toward each other by tightening the band in the single loop. The plurality of spaces among the trabeculae may be located along walls of the ventricle of the heart. Accordingly, the method of improving cardiac function may comprise pulling the walls of the ventricle of the heart inwards by tightening the band in the single loop and locking the band in the loop.

In some embodiments, the at least one catheter may be pre-shaped to pass through the plurality of spaces among the trabeculae, to thereby aid in guiding the band through the plurality of spaces among the trabeculae. In some embodiments, locking the band in the loop may include passing a pull-string through the band, pulling at least one end of the pull-string through the at least one catheter to tighten the band, and locking the pull-string into the loop. The pull-string may be a self-locking pull-string.

In yet another embodiment of the present disclosure, tightening the band in a single loop may include tightening the band until the loop reaches a predefined circumference. For example, the circumference of the loop after tightening the band may be smaller than the circumference of the loop before tightening the band. In some embodiments, the method may further comprise tightening the band in the single loop to draw the plurality of papillary muscles into contact with each other.

In accordance with the present disclosure, looping the at least one guidewire through the plurality of spaces among the trabeculae may include passing the at least one guidewire through a steerable catheter and modifying a shape of the steerable catheter through the plurality of spaces among the trabeculae, thereby looping the guidewire through the plurality of spaces among the trabeculae.

The transcatheter papillary muscle sling procedure described herein, which involves passing a band through spaces among the ventricular trabeculae and then tightening the band to pull the papillary muscles closer to each other, may provide both papillary muscle repositioning and ventriculoplasty in a single procedure. The relative amount of papillary muscle repositioning and ventriculoplasty achieved depends on the position of the band relative to the papillary muscles.

Additional objects and advantages of the embodiments will be set forth in part in the description that follows, and in part will be obvious from the description or may be learned by practice of the embodiments. The objects and advantages of the embodiments will be realized and attained by means of the elements and combinations particularly pointed out in the appended claims.

It is to be understood that both the foregoing general description and the following detailed description are exemplary and explanatory only and are not restrictive of the claims.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 4A-4C illustrate an exemplary method of directing, using a guidewire, a band around a plurality of papillary muscles in accordance with the embodiments of the present disclosure;

DETAILED DESCRIPTION OF EMBODIMENTS

The present disclosure relates to methods and devices for improving cardiac function. While the present disclosure provides examples of improving cardiac function by looping a band around the plurality of papillary muscles, it should be noted that aspects of the disclosure in their broadest sense, are not limited to looping a band around the plurality of papillary muscles. Rather, it is contemplated that the forgoing principles may be applied to other methods of improving cardiac function as well. The term band refers generally to any element that is capable of either partially or completely encircling a plurality of papillary muscles in the ventricle of the heart in order to bring the papillary muscles closer to each other. Looping a band around the plurality of papillary muscles, as illustrated in FIGS. 4A-4C, is one example of a method of improving cardiac function in accordance with the present disclosure. Looping may involve partially or completely surrounding one or more papillary muscles.

Figure 1:
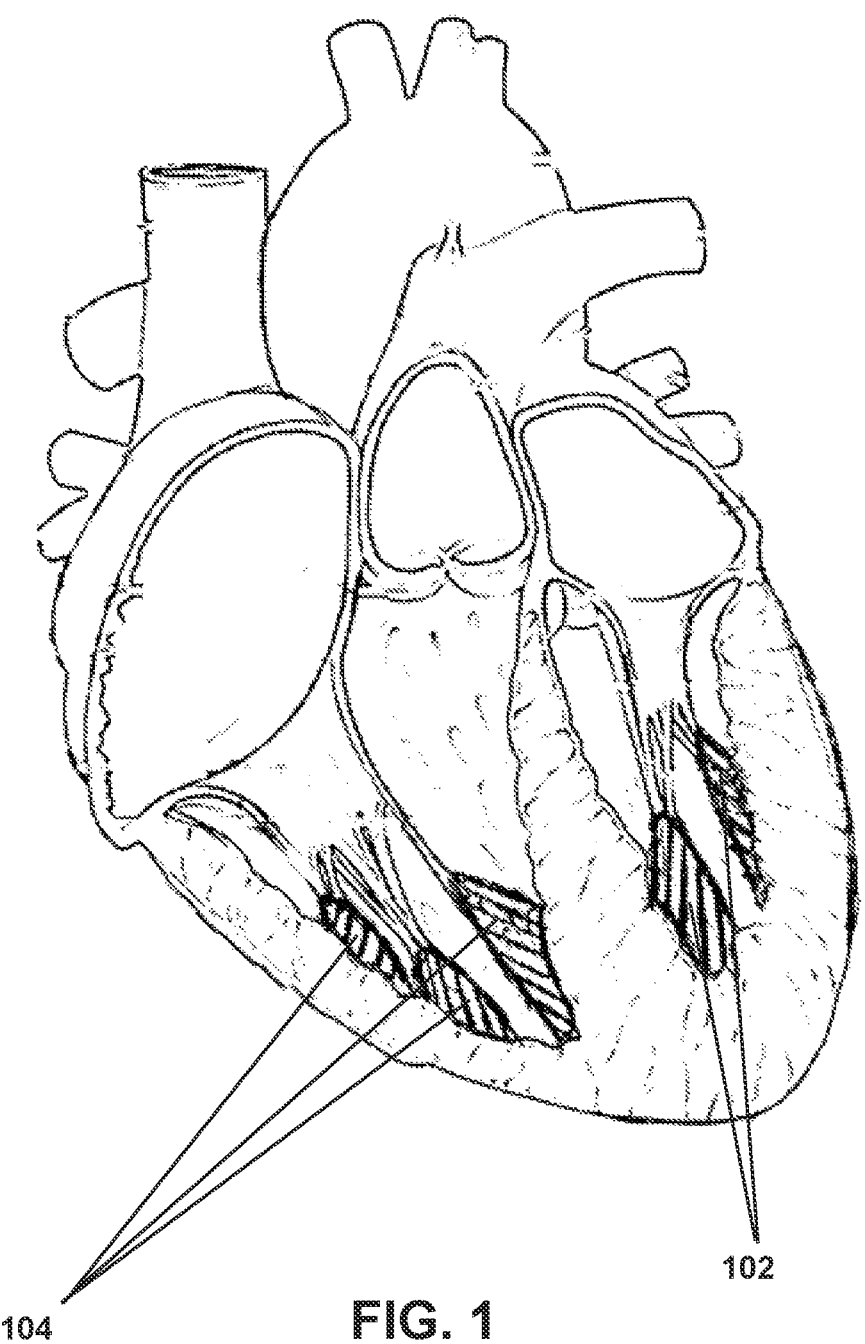
FIG. 1 illustrates an exemplary anatomy of a human heart in which embodiments of the present disclosure may be employed.
Figure 2A:
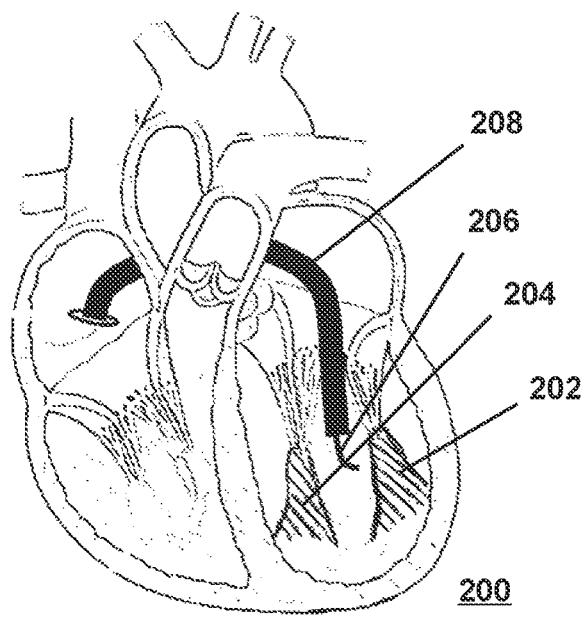
FIGS. 2A-2C illustrate an exemplary method of introducing a guidewire into the ventricle of the heart and looping the guidewire around the plurality of papillary muscles in accordance with the embodiments of the present disclosure.
Figure 2B:
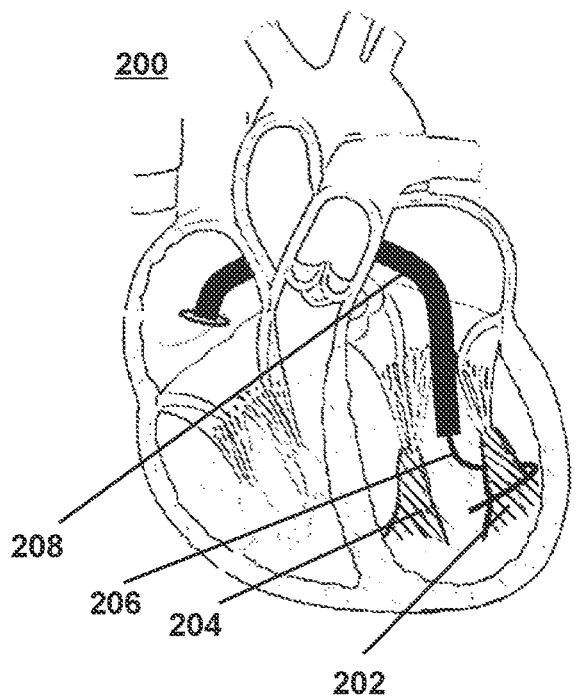
Figure 2C:
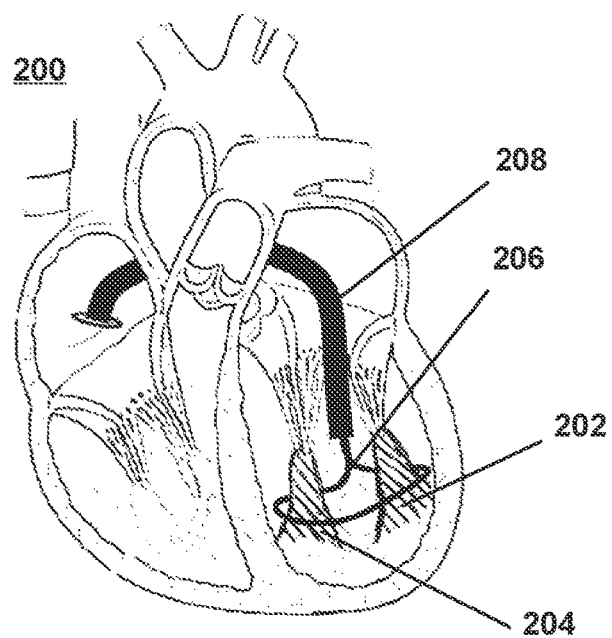
Figure 3A:
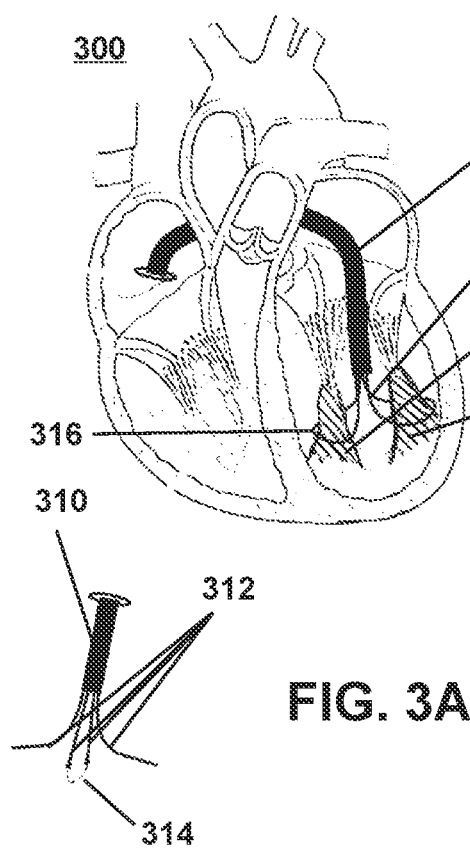
FIGS. 3A-3C illustrate exemplary connections used to interconnect a first guidewire and a second guidewire in accordance with the embodiments of the present disclosure.
Figure 3B:
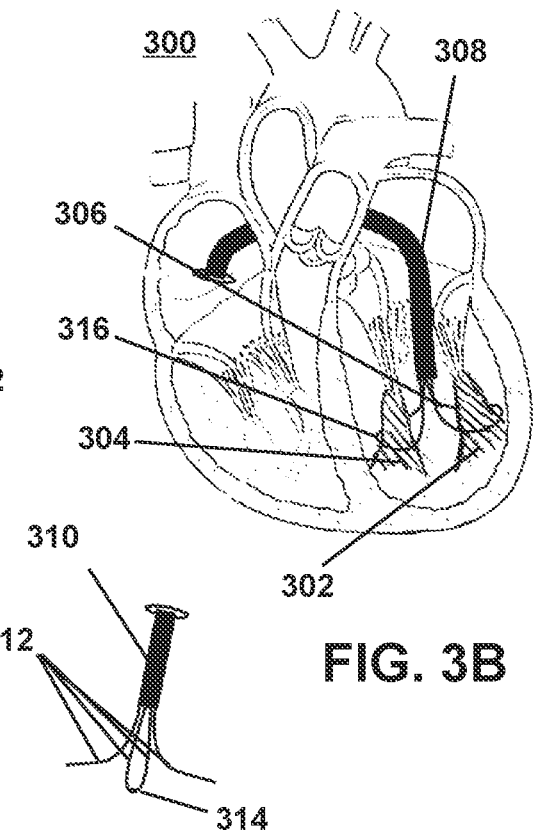
Figure 3C:
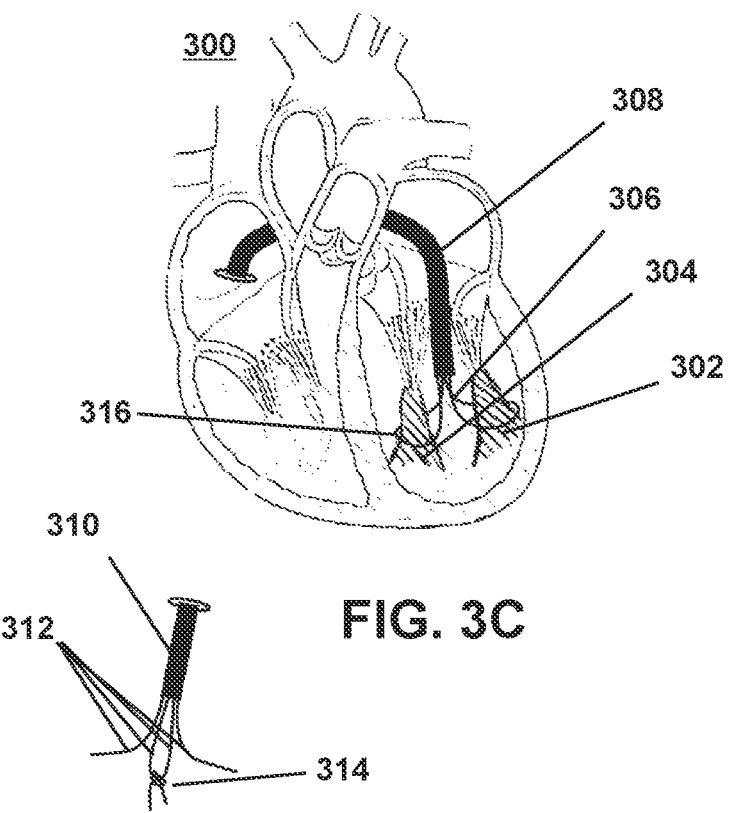

A method of improving cardiac function in accordance with the present disclosure may include transcatheterly delivering at least one guidewire to a ventricle in a heart. The term "transcatheterly" may include delivering via a catheter. FIGS. 2A-2C, for example, illustrates a single catheter 208 used to deliver at least one guidewire 206 to a ventricle in a heart. A transcatheter approach to the ventricle of the heart may be transthoracic, transarterial, transvenous, transseptal, transapical, or transatrial. All of these can be achieved using standard medical catheters and catheterization tools known in the art. They may also be performed using new tools for performing associated functions. The term "guidewire" may include any thin elongated, flexible member that is capable of encircling a plurality of papillary muscles in the ventricle of the heart. FIGS. 2A-2C, for example, illustrate a guidewire 206 for encircling, i.e. completely or partially surrounding, a plurality of papillary muscles 202 and 204. The guidewire 206 may be a string, a thread, a wire, a suture, a coil, or other thin elongated flexible member suitable for use within an anatomical body. The forgoing principles are in no way limited to a single guidewire. Rather, it is contemplated that the forgoing principles may be applied to methods using one or more guidewires. For example, FIGS. 3A-3C illustrate two guidewires 306 encircling a first papillary muscle 302 and a second papillary muscle 304. In addition, while the disclosure describes inventive concepts in connection with the mitral valve, in its broadest sense, the invention is not so limited and can be used for any papillary muscles, whether in the left ventricle or the right ventricle as shown, for example, in FIG. 1.

In accordance with the present disclosure, a method may further include looping the at least one guidewire around a plurality of papillary muscles in the ventricle. In some embodiments of the present disclosure, the plurality of papillary muscles in the ventricle may include two and/or three papillary muscles. As seen in FIG. 1, there are generally two papillary muscles 102 in the left ventricle of the heart and three papillary muscles 104 in the right ventricle of the heart. Therefore, the plurality of papillary muscles may include two and/or three papillary muscles.

Figure 6A:
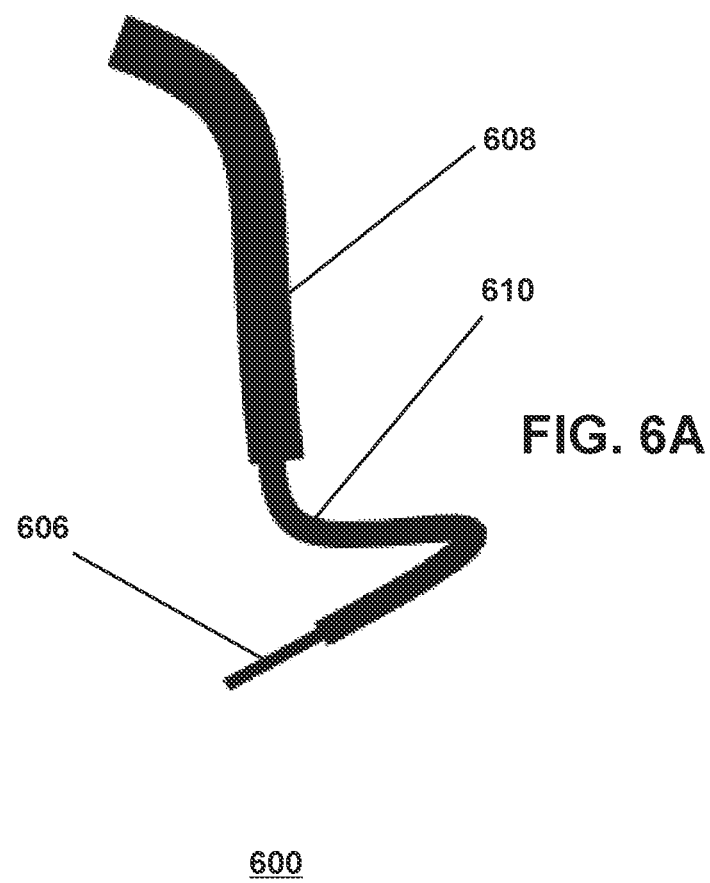
FIGS. 6A-6B illustrate an exemplary pre-shaped catheter to facilitate positioning a guidewire around the papillary muscles in accordance with the embodiments of the present disclosure.
Figure 6B:
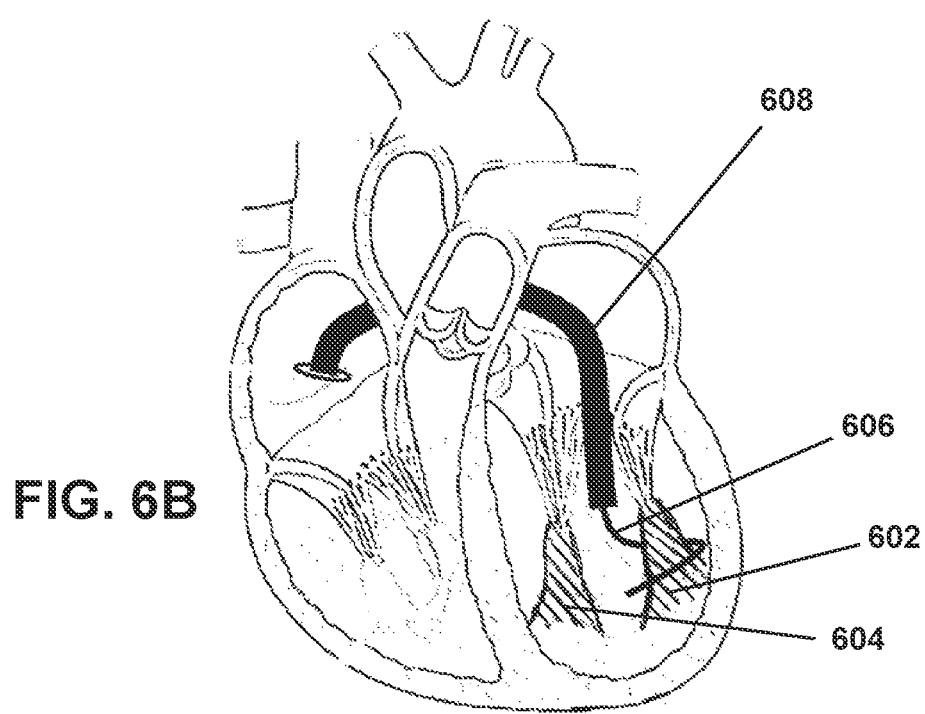

In some embodiments in accordance with the present disclosure, looping the at least one guidewire around the plurality of papillary muscles in the ventricle may include using a pre-shaped catheter whose shape aids in looping the guidewire around the papillary muscles. For example, as illustrated in FIGS. 6A-6B, a pre-shaped catheter 610 may aid in looping a guidewire 606 around the papillary muscles 602 and 604. For example, the catheter may be made of a shape memory material that enables the catheter to assume the pre-shape following release from a sheath (not shown).

In other embodiments, looping the at least one guidewire around the plurality of papillary muscles in the ventricle may include using a steerable catheter whose shape can be modified interactively by the user to aid in looping the guidewire around the papillary muscles. In yet another embodiment, looping the at least one guidewire around the plurality of papillary muscles may include looping a first guidewire around a first papillary muscle, looping a second guidewire around a second papillary muscle, and interconnecting the first guidewire and the second guidewire to thereby create a single loop around the plurality of papillary muscles. In other embodiments, looping the guidewire around the papillary muscles may include using a pre-shaped and/or steerable guidewire to aid in looping the guidewire around the papillary muscles. Looping the guidewire around the plurality of papillary muscles may also be performed by any other mechanism for steering at least one guidewire around one or more papillary muscles. The at least one guidewire may include a single guidewire looped around a group of papillary muscles, or multiple guidewires that are later interconnected, after looping less than all papillary muscles, to form a loop around a plurality of papillary muscles.

The papillary muscles, around which the looping occurs, may include chordae or base portions of the muscles to which chordae are attached. The papillary muscles, around which the looping occurs, may include multiple papillary muscle heads or multiple papillary muscle bodies. In some embodiments, the papillary muscles, around which the looping occurs, may include trabeculae of the papillary muscles. For example, looping the guidewire around the papillary muscles may include passing the guidewire through the plurality of spaces among the trabeculae between the papillary muscles and a wall of the ventricle.

In some embodiments, the looping may occur through the plurality of spaces among the trabeculae to thereby pull the plurality of papillary muscles closer to each other. The plurality of spaces among the trabeculae may be located along the walls of the ventricle of the heart. Accordingly, guiding the band through the plurality of spaces among the trabeculae and tightening the band in a single loop may pull the walls of the ventricle of the heart inwards, thereby pulling the papillary muscles closer to each other.

Figure 8:
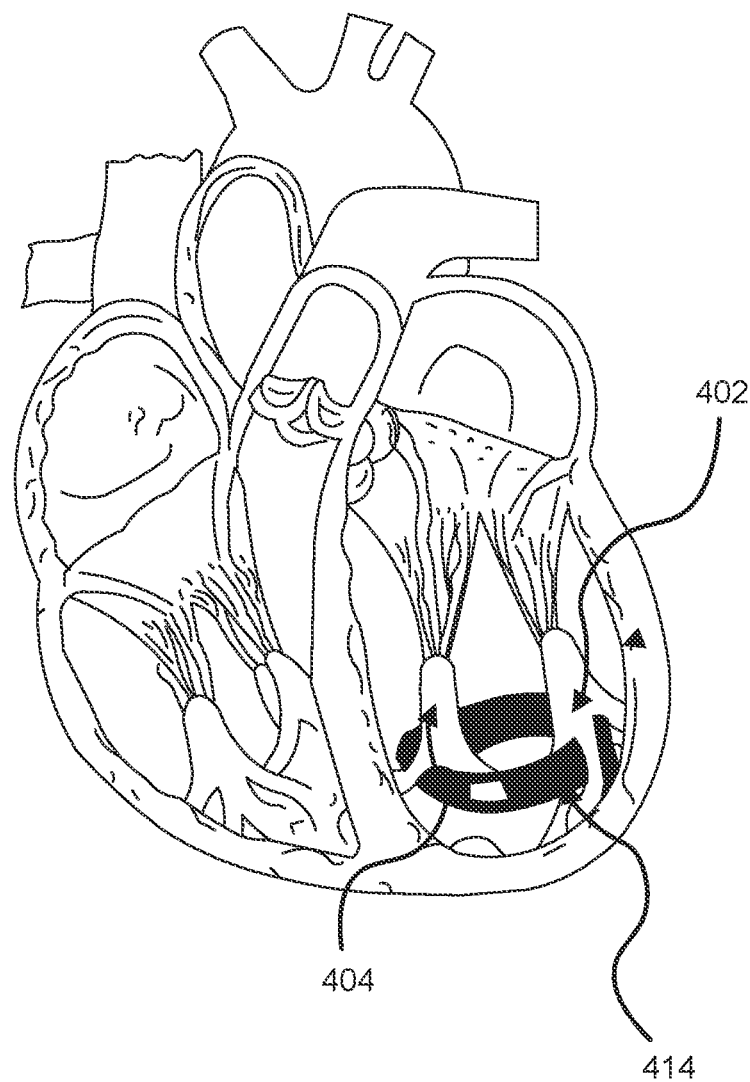
FIG. 8 illustrates an exemplary method of passing a band through spaces among a trabeculae in accordance with the embodiments of the present disclosure.

Embodiments of the present disclosure may further include directing, using the guidewire, a band around the plurality of papillary muscles. In some embodiments, the band may also be directed, using the guidewire, through the plurality of spaces among the trabeculae. Directing, using the guidewire, the band around the plurality of papillary muscles may include directing the band such that the band at least partially encircles between two and three papillary muscles simultaneously. For example, as seen in FIGS. 4A-4C, the guidewire 406 may be used to direct the band 414 such that the band 414 at least partially encircles a plurality of papillary muscles 402 and 404. In other embodiments, as seen in FIG. 8, directing the band 414 around the plurality of papillary muscles 402 and 404 may include passing the band 414 through the spaces among the trabeculae between the plurality of papillary muscles 402 and 404 and the wall of the ventricle of the heart. In yet another embodiment, directing the band 414 around the plurality of papillary muscles 402 and 404 may include passing the band 414 through the spaces among the trabeculae along the walls of the ventricle of the heart.

In some embodiments, the band may be a tube. The tube may be hollow inside. Accordingly, in some embodiments, directing the band around the plurality of papillary muscles may include passing a band that is formed of a tube over the guidewire. In other embodiments of the present disclosure, a portion of the tube may include a tube and/or a ring. In other embodiments, a portion of the tube may be connected to a tube and/or a ring. As such, directing the band around the plurality of papillary muscles may include directing a band, a portion of which is a tube and/or a ring or that is connected to a tube and/or a ring, along a guidewire by passing the tube and/or the ring portion over the guidewire. In yet another embodiment, directing the band around the plurality of papillary muscles may include connecting an end of the band to an end of the guidewire and pulling on the other end of the guidewire such that pulling the guidewire around the plurality of papillary muscles will pull the band around the papillary muscles as well. Alternatively, the band may be sized to simultaneously encircle a plurality of papillary muscles and pull the plurality of papillary muscles toward each other. For example, as seen in FIGS. 5A-5D, the band 506 may be sized to simultaneously encircle both of the papillary muscles 502 and 504.

According to some embodiments of the present disclosure, the band placed around the plurality of papillary muscles may be formed of a stent-like frame within a tube. The tube may be made of a fabric or other flexible material. The stent-like frame may be able to expand after deployment from a catheter. In other embodiments, the stent-like frame may be expanded by the use of an inflatable balloon. For example, the inflatable balloon may have a predefined shape upon expansion and may induce the stent-like frame to bend into the shape of a balloon. In alternate embodiments, the stent-like frame may be self-expanding and may have a predefined shape into which it self-expands upon deployment from the catheter or from a sheath intended to maintain it in its compressed configuration.

In some embodiments of the present disclosure, the band includes at least one of polytetrafluoroethylene (PTFE), expanded polytetrafluoroethylene (ePTFE), Dacron, and/or any other biologically inert synthetic material with appropriate tensile strength for use in pulling the papillary muscles closer together. In other embodiments, the band may be manufactured by extrusion, knitting, weaving, braiding, or any other method of forming the biologically inert synthetic material into a band or a tubular band. In some embodiments the band may be elastic or non-elastic or partially elastic. In other embodiments, a part of the band may be elastic and a part of the band may be non-elastic. According to some embodiments of the present disclosure, the band may be made of more than one material. That is, a part of the band may be made of one material while another part of the band may be made of a different material. In yet another embodiment, the band may be made of biological material from the patient, from another human donor, or from animal derived material.

Figure 7:
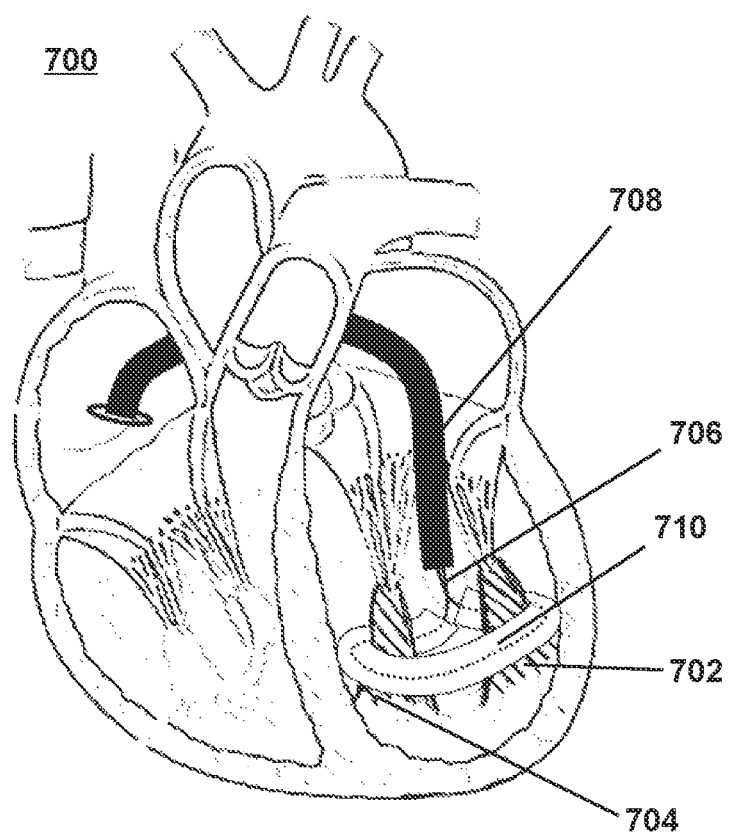
FIG. 7 illustrates an exemplary method of tightening a band around the papillary muscles using a pull-string in accordance with the embodiments of the present disclosure.

According to various exemplary embodiments of the present disclosure, tightening the band in a single loop around the plurality of papillary muscles to pull the plurality of papillary muscles toward each other may include passing a pull-string through the band, pulling the ends of the pull-string through a catheter to tighten the band, and using a transcatether suture lock to lock the pull-string into a loop of a desired and/or appropriate size. For example, as illustrated in FIG. 7, a pull-string 706 may be passed through the band 710 to tighten the band 710 in a single loop around the plurality of papillary muscles 702 and 704. The ends of the pull-string 706 may be pulled through the catheter 708 in order to tighten the band 710 around the papillary muscles 702 and 704. In other embodiments, tightening the band in a single loop around the plurality of papillary muscles may include passing a self-locking pull string through the band and pulling one or both ends of the pull-string to tighten the band around the plurality of papillary muscles. Pulling one or both ends of the pull-string may cause the pull-string to self-lock into a loop of the appropriate size. In another embodiment of the present disclosure, tightening the band in a single loop around the plurality of papillary muscles may include pulling a plurality of pull-strings attached to both ends of the band through a catheter. Pulling the plurality of pull-strings attached may tighten the band. Using a transcatheter suture lock, the pull-string may be locked into place, thereby forming the band into a loop of an appropriate and/or desired size.

The pull-string may be self-locking or the pull-string may be locked using another locking mechanism. In some embodiments, the pull-string may be coupled to any mechanism capable of locking the band into a looped configuration. In some embodiments of the present disclosure, a self-locking pull-string may be similar in construction to a beaded locking cable tie, in which a string includes one or more beads in fixed positions along the length of the string. As the beads pass through a locking grasper, the string and/or the band may be locked into a fixed position because the beads will not be able to pass in the opposite direction as it passes through the locking grasper. The self-locking pull-string may be locked at a position, at which the papillary muscles are pulled towards each other in order to reposition the papillary muscles.

Figure 5A:
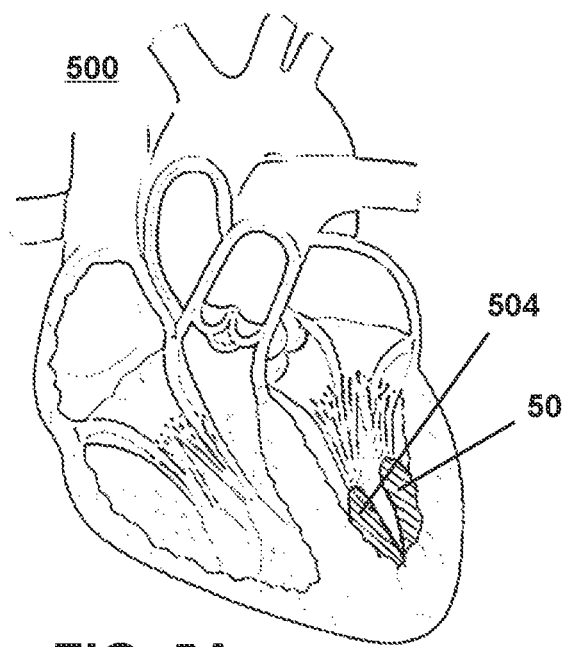
FIGS. 5A-5D illustrate an exemplary method of tightening a band around a plurality of papillary muscles in accordance with the embodiments of the present disclosure.
Figure 5B:
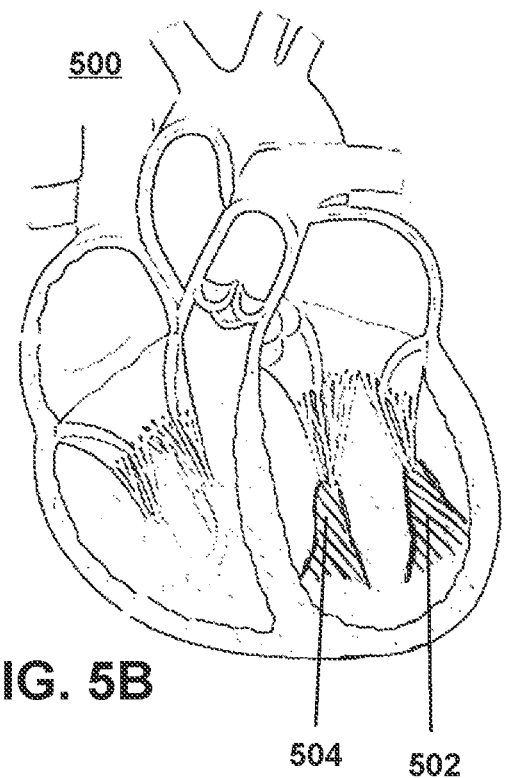
Figure 5C:
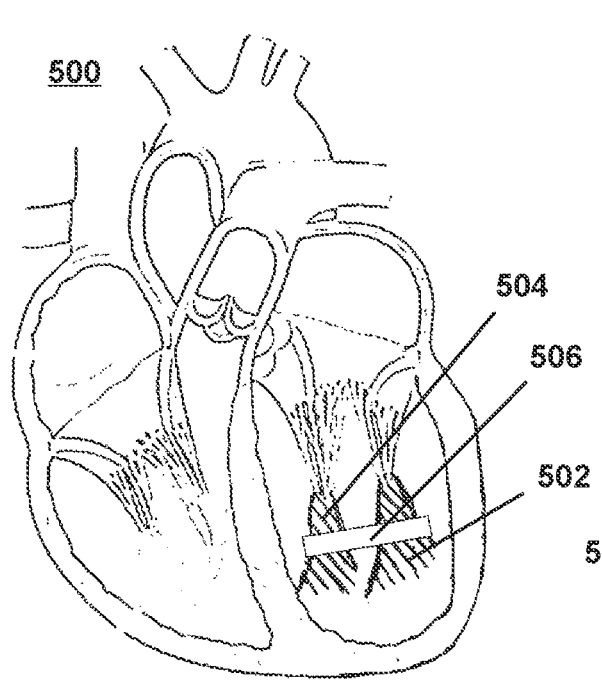
Figure 5D:
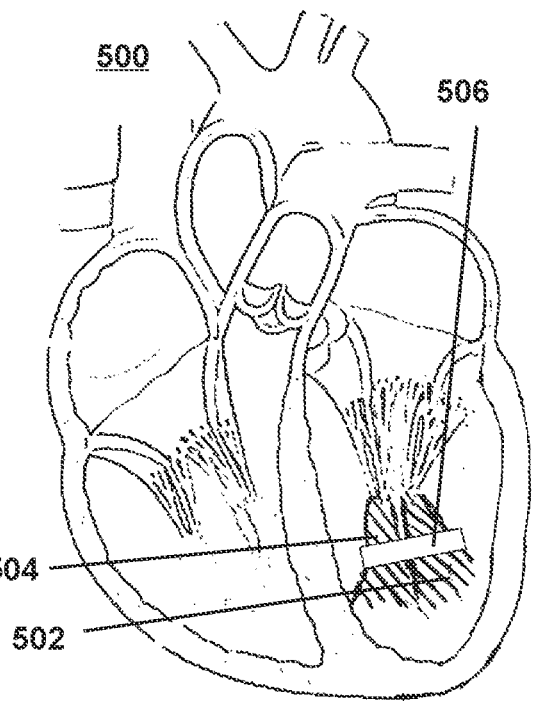

In some embodiments, pulling the plurality of papillary muscles toward each other may include pulling the plurality of papillary muscles until the opposing surfaces of each of the papillary muscles are in contact with each other. In other embodiments, pulling the plurality of papillary muscles toward each other may include pulling the papillary muscles so that the opposing surfaces of each of the papillary muscles are closer to each other than they were before. In yet another embodiment, pulling the papillary muscles toward each other may include pulling the papillary muscles until the distance between the opposing surfaces of each papillary muscle meets a certain predetermined value or range of values. For example, the papillary muscles may be pulled until the distance between the opposing surfaces of each of the papillary muscles is less than a predetermined distance or within a predetermined range of a predetermined distance. According to another embodiment of the present disclosure, pulling the papillary muscles toward each other may include pulling the papillary muscles so that the loop formed by the band around the papillary muscles has a predetermined circumference. For example, FIG. 5A illustrates a normal heart with properly positioned papillary muscles. In contrast, FIG. 5B illustrates a heart with dilated cardiomyopathy exhibiting an enlarged ventricle and displaced papillary muscles 502 and 504. As such, a band 506 may be looped around the papillary muscles 502 and 504 in order to pull them closer to each other, for example, as illustrated in FIG. 5C. In another example, the plurality of papillary muscles 502 and 504 may be pulled towards each other until the opposing surfaces of each of the papillary muscles 502 and 504 are in contact with each other, as illustrated in FIG. 5D.

The present disclosure further relates to methods and devices for transcatheterly delivering a band to at least partially encircle a plurality of papillary muscles in a heart of a body. While the present disclosure provides examples of delivering a first guidewire and a second guidewire to the ventricle via at least one catheter, it should be noted that aspects of the disclosure in their broadest sense, are not limited to delivering two guidewires to the ventricle. Rather, it is contemplated that the forgoing principles may be applied to delivering fewer or more guidewires to the ventricle of the heart via a catheter. The term band refers generally to any element that is capable of at least partially encircling a plurality of papillary muscles in the ventricle of the heart in order to bring the papillary muscles closer to each other. Encircling may involve partially or completely surrounding one or more papillary muscles. Delivering a first guidewire and a second guidewire to the ventricle of the heart, as illustrated in FIGS. 3A-3C, is one example of a method of delivering a band to at least partially encircle a plurality of papillary muscles 302 and 304 in a heart of the body in accordance with the present disclosure.

The method of transcatheterly delivering a band to at least partially encircle one or more papillary muscles in a heart of the body may comprise transcutaneously inserting at least one catheter into a ventricle of the heart. The transcatheter approach to the ventricle may be transthoracic, transarterial, transvenous, transseptal, transapical, or transatrial. Each of these transcatheter approaches can be achieved using medical catheters and catheterization tools known in the art. They may also be performed using new tools for performing associated functions. In addition, while the disclosure describes inventive concepts in connection with the mitral valve, in its broadest sense, the invention is not so limited and can be used for any papillary muscles, whether in the left ventricle or the right ventricle.

The method may further comprise delivering a first guidewire to the ventricle via the at least one catheter. In some embodiments, the first guidewire may include a string, thread, wire, suture, coil, or any other thin, elongated, flexible, and/or biocompatible member.

According to an embodiment of the present disclosure, the method may further comprise looping the first guidewire around a first papillary muscle. For example, as illustrated in FIGS. 3A-3C, a first guidewire 306 may be delivered to the ventricle via at least one catheter 308 such that it at least partially encircles a first papillary muscle 302. In some embodiments, looping the first guidewire around the first papillary muscle may include using a pre-shaped catheter whose shape aids in looping around papillary muscles. For example, as seen in FIGS. 6A-6B, the catheter 610 may be pre-shaped to facilitate looping the first guidewire 606 around the first papillary muscle 602. In another embodiment, looping the first guidewire around the first papillary muscle may include using a steerable catheter whose shape can be modified interactively by the user to aid in looping around the papillary muscles. Looping may involve partially or completely surrounding one or more papillary muscles.

According to an embodiment of the present disclosure, the method may further comprise bringing a first end of the first guidewire out of the body. That is, a first end of the first guidewire may be out of the body while a second end of the first guidewire remains inside the body. In other embodiments, both ends of the first guidewire may be brought outside of the body, while in yet other embodiments the first end of the first guidewire may be brought out of the body while a second end of the first guidewire remains outside the body never having entered the body. For example, as illustrated in FIGS. 3A-3C, both ends 312 of the first guidewire 306 may be brought through a proximal end 310 of the catheter 308 and outside of the body. In other embodiments, bringing the first end of the first guidewire out of the body may include pushing the second end of the first guidewire such that the first end of the first guidewire is pushed through the catheter and out of the body. In other embodiments, bringing the first end of the first guidewire out of the body may include catching the first end of the first guidewire within the ventricle of the heart by a guidewire catching technique. For example, a magnetic guidewire catching may be implemented, wherein a magnet is used to catch the first end of the first guidewire and pull the first end of the first guidewire out of the body. While the forgoing principles describe a magnetic guidewire catching mechanism, any mechanism capable of catching the first end of the guidewire and pulling the guidewire out of the body may be used. For example, a capture loop guidewire catching mechanism, a guidewire catching basket, or any combination thereof may be used to bring the first end of the first guidewire out of the body. Bringing the first end of the first guidewire out of the body may further include passing the guidewire from one portion of a catheter to another portion of the catheter such that the guidewire is captured at the second portion of the catheter. Once the guidewire is captured at the second portion of the catheter, the catheter may be pulled out of the body in order to bring the first end of the first guidewire out of the body.

The method may further comprise delivering a second guidewire to the ventricle via the at least one catheter. In some embodiments, the second guidewire may also include a string, thread, wire, suture, coil, or any other thin, elongated, flexible, and/or biocompatible member.

According to an embodiment of the present disclosure, the method may further comprise looping the second guidewire around a second papillary muscle. For example, as illustrated in FIGS. 3A-3C, a second guidewire 316 may be delivered to the ventricle via at least one catheter 308 such that it encircles a second papillary muscle 304. In some embodiments, looping the second guidewire around the second papillary muscle may include using a pre-shaped catheter whose shape aids in looping around papillary muscles. For example, the catheter may be pre-shaped to facilitate looping the second guidewire around the second papillary muscle. For example, as seen in FIGS. 6A-6B, the catheter 610 may be pre-shaped to facilitate looping a second guidewire (not shown) around the second papillary muscle 604. In another embodiment, looping the second guidewire around the second papillary muscle may include using a steerable catheter whose shape can be modified interactively by the user to aid in looping around the papillary muscles.

According to an embodiment of the present disclosure, the method may further comprise bringing a second end of the second guidewire out of the body. That is, a second end of the second guidewire may be out of the body while the other end of the second guidewire remains inside the body. In another embodiment, both ends of the second guidewire may be brought outside of the body, while in yet another embodiment a second end of the second guidewire may be brought out of the body while the other end of the second guidewire remains outside the body, never having entered the body. For example, both ends 312 of the second guidewire 316 may be brought outside the body through a proximal end 310 of the catheter 308. Bringing the second end of the second guidewire out of the body may include pushing the first end of the second guidewire such that the second end of the second guidewire is pushed through the catheter and out of the body. In other embodiments, bringing the second end of the second guidewire out of the body may include catching the second end of the second guidewire within the ventricle of the heart by a guidewire catching technique. For example, a magnetic guidewire catching may be implemented, wherein a magnet is used to catch the second end of the second guidewire and pull the second end of the second guidewire out of the body. While the forgoing principles describe a magnetic guidewire catching mechanism, any mechanism capable of catching the second end of the guidewire and pulling the guidewire out of the body may be used. For example, a capture loop guidewire catching mechanism, a guidewire catching basket, or any combination thereof may be used to bring the second end of the second guidewire out of the body. Bringing the second end of the second guidewire out of the body may further include passing the guidewire from one portion of a catheter to another portion of the catheter such that the guidewire is captured at the second portion of the catheter. Once the guidewire is captured at the second portion of the catheter, the catheter may be pulled out of the body in order to bring the second end of the second guidewire out of the body.

According to an embodiment of the present disclosure, the method may further comprise interconnecting the first guidewire to the second guidewire. Interconnecting the first guidewire to the second guidewire may include tying the first guidewire and the second guidewire together. In other embodiments, interconnecting the first and second guidewires may include connecting the first and second guidewires together with a built-in connector, or any other type of connector used to connect a plurality of ropes, strings, wires, or cables together. In some embodiments, interconnecting the first and second guidewires may include connecting the first and second guidewires with an applied clip, clasp, or any other type of clip, clasp, or crimp ring used to connect a plurality of ropes, strings, wires, or cables together. For example, as illustrated in FIGS. 3A-3C, one end of the first guidewire 306 and one end of the second guidewire 316 may be interconnected using a flexible connector (FIG. 3A), using a rigid connector (FIG. 3B), tying a knot (FIG. 3C), or any combination thereof. In other embodiments, the ends of the first and/or second guidewires may be interconnected using any mechanism used to connect a plurality of ropes, strings, wires, or cables together.

Consistent with the embodiments of the present disclosure, the method may further comprise pulling at least one end of the first and second guidewires after interconnecting them to thereby establish a single loop around at least the first papillary muscle and the second papillary muscle. For example, as illustrated in FIGS. 4A-4C, one end of a guidewire 412b may be pulled through a proximal end 410 of a catheter 408 in order to establish a single loop 406 around at least the first papillary muscle 402 and the second papillary muscle 404. The papillary muscles, around which the looping occurs, may include chordae or base portions of the muscles to which chordae are attached. In some embodiments, the papillary muscles, around which the looping occurs, may include multiple papillary muscle heads or multiple papillary muscle bodies. In some embodiments, the papillary muscles, around which the looping occurs, may include trabeculae of the papillary muscles. In yet another embodiment, the trabeculae may be located along walls of the ventricle of the heart. For example, looping the first and second guidewires around the papillary muscles may include passing the first and second guidewires through the plurality of spaces among the trabeculae between the papillary muscles and a wall of the ventricle.

In some embodiments, the method may further comprise directing, using the single loop established by pulling the at least one end of the first and second guidewires after interconnecting them, a band around the first papillary muscle and the second papillary muscle. According to some embodiments of the present disclosure, the band may be a tube positioned over the guidewire. In other embodiments, only a portion of the band may be a tube or a ring. In yet another embodiment, a portion of the band may be connected to a tube or a ring. As such, directing the band around the first and second papillary muscles may include directing a band along a guidewire by passing the tube or ring portion over the guidewire. In other embodiments, directing the band around the first and second papillary muscles may include connecting an end of the band to an end of the guidewire and pulling on the other end of the guidewire such that the guidewire pulls the band around the papillary muscles. For example, as illustrated in FIGS. 4A-4C, an end of the band 414 may be connected to an end of the guidewire 412a. The other end of the guidewire 412b may be pulled through a proximal end 410 of the catheter 408 in order to pull the band 414 through the catheter 408 and around the papillary muscles 402 and 404. The band 414 may form a single loop around at least the first papillary muscle 402 and the second papillary muscle 404, as illustrated in FIG. 4C.

According to another embodiment of the present disclosure, the band may be sized to simultaneously encircle, i.e. completely or partially surround, a plurality of papillary muscles and pull the plurality of papillary muscles toward each other. For example, as seen in FIGS. 5C and 5D, the band 506 may be sized to simultaneously encircle a first papillary muscle 502 and a second papillary muscle 504. Alternatively, the band may be a tube or a portion of the band may be a tube. For example, a first portion of the band may be a tube whereas a second portion of the band may not be a tube. In some embodiments of the present disclosure, the band may include at least one of polytetrafluoroethylene (PTFE), expanded polytetrafluoroethylene (ePTFE), Dacron, and/or any other biologically inert synthetic material with appropriate tensile strength for use in pulling the papillary muscles closer together. In other embodiments, the band may be manufactured by extrusion, knitting, weaving, braiding, or any other method of forming the biologically inert synthetic material into a band or a tubular band. In some embodiments the band may be elastic or non-elastic or partially elastic. In other embodiments, a part of the band may be elastic and a part of the band may be non-elastic. According to some embodiments of the present disclosure, the band may be made of more than one material. That is, a part of the band may be made of one material while another part of the band may be made of a different material. In yet another embodiment, the band may be made of biological material from the patient, from another human donor, or from animal derived material.

In some embodiments of the present disclosure, the method of interconnecting the first guidewire and the second guidewire may include connecting a first end of the first guidewire to a second end of the second guidewire outside of the body. In other embodiments, the first guidewire may be connected to the second guidewire inside of the body. In other embodiments of the present disclosure, bringing at least one of the first end of the first guidewire and the second end of the second guidewire out of the body may include catching at least one of the first end and the second end using a magnet and pulling at least one of the first and second end out of the body. While the forgoing principles describe a magnetic guidewire catching mechanism, any mechanism capable of catching at least one of the first end of the first guidewire and the second end of the second guidewire and pulling at least one of the first guidewire and the second guidewire out of the body may be used. For example, a capture loop guidewire catching mechanism, a guidewire catching basket, or any combination thereof may be used to bring the second end of the second guidewire out of the body. Bringing at least one of the first end of the first guidewire and the second end of the second guidewire out of the body may include pushing a second end of the first guidewire, thereby causing the first end of the first guidewire to move through the at least one catheter and out of the body. In other embodiments, bringing at least one of the first end of the first guidewire and the second end of the second guidewire out of the body may include passing at least one of the first end of the first guidewire and the second end of the second guidewire around a papillary muscle from a first portion of the at least one catheter to a second portion of the catheter and capturing at least one of the first and second guidewires at the second portion of the catheter. Once the first guidewire and/or the second guidewire is captured at the second portion of the catheter, the catheter may be pulled out of the body in order to extract at least one of the first end of the first guidewire and the second end of the second guidewire from the body.

According to another embodiment of the present disclosure, the method of transcatheterly delivering a band to at least partially encircle a plurality of papillary muscles in the heart may comprise delivering an end of a third guidewire to the heart ventricle via the at least one catheter, looping the end of the third guidewire around a third papillary muscle, bringing the end of the third guidewire out of the body while the third guidewire remains looped around the third papillary muscle, and interconnecting at least one of the first and second guidewires with the third guidewire. Therefore, in some embodiments, the first, second, and third guidewires may direct a band in a single loop around three papillary muscles.

The method of transcatheterly delivering a band to at least partially encircle a plurality of papillary muscles in the heart may further comprise connecting an end of the band to at least one of the first and second guidewire, and pulling the proximal end of the guidewire while the guidewire is looped around the first and second papillary muscles, thereby guiding the band around the first and second papillary muscles. For example, as illustrated in FIGS. 4A-4C, an end of the band 414 may be connected to an end of the guidewire 412a. The other end of the guidewire 412b may be pulled through a proximal end 410 of the catheter 408 in order to pull the band 414 through the catheter 408 and around the papillary muscles 402 and 404.

In order to interconnect the first guidewire and the second guidewire, at least one of the first guidewire and the second guidewire may include a built-in connector. As such, an end of the first guidewire may be connected to an end of the second guidewire via the built-in connector. While the forgoing embodiment describes a built-in connector, any other type of connector used to connect a plurality of ropes, strings, wires, or cables together may be used. For example, in some embodiments, interconnecting the first and second guidewires may include connecting the first and second guidewires with an applied clip, clasp, or any other type of clip, clasp, or crimp ring used to connect a plurality of ropes, strings, wires, or cables together. For example, as illustrated in FIGS. 3A-3C, one end of the first guidewire 306 and one end of the second guidewire 316 may be interconnected using a flexible connector (FIG. 3A), using a rigid connector (FIG. 3B), tying a knot (FIG. 3C), or any combination thereof. In other embodiments, the ends of the first and/or second guidewires may be interconnected using any mechanism used to connect a plurality of ropes, strings, wires, or cables together.

Another embodiment of the present disclosure relates to methods and devices for improving cardiac function. While the present disclosure provides examples of improving cardiac function by looping a single band around the plurality of papillary muscles, it should be noted that aspects of the disclosure in their broadest sense, are not limited to looping a band around the plurality of papillary muscles. Rather, it is contemplated that the forgoing principles may be applied to other methods of improving cardiac function as well. The term band refers generally to any element that is capable of encircling a plurality of papillary muscles in the ventricle of the heart in order to bring the papillary muscles closer to each other. Looping a band around the plurality of papillary muscles, as illustrated in FIGS. 4A-4C and 5A-5D, is one example of a method of improving cardiac function in accordance with the present disclosure. Looping may involve partially or completely surrounding one or more papillary muscles.

A method of improving cardiac function in accordance with the present disclosure may include transcatheterly looping a single band around a plurality of papillary muscles in a ventricle of a heart. The term "transcatheterly" may include delivering via a catheter. FIGS. 4A-4C, for example, illustrates a single catheter 408 used to deliver and loop a single band 414 around a plurality of papillary muscles 402, 404 in a ventricle of a heart. A transcatheter approach to the ventricle of the heart may be transthoracic, transarterial, transvenous, transseptal, transapical, or transatrial. All of these can be achieved using standard medical catheters and catheterization tools known in the art. They may also be performed using new tools for performing associated functions. In addition, while the disclosure describes inventive concepts in connection with the mitral valve, in its broadest sense, the invention is not so limited and can be used for any papillary muscles, whether in the left ventricle or the right ventricle.

In accordance with the present disclosure, the method may further include looping a single band around a plurality of papillary muscles in a ventricle of a heart such that the band at least partially encircles a cluster of papillary muscles. The term "cluster" generally refers to a plurality of papillary muscles that are relatively in close proximity to each other. For example, the "cluster" of papillary muscles may include two and/or three papillary muscles. The "cluster" may also refer to any subset of two or more papillary muscles within a single ventricle of the heart. The cluster may have an outer peripheral boundary defined by the at least partially encircling band. Further, the cluster may have an inner region on sides of the plurality of papillary muscles opposite the outer peripheral boundary. For example, as illustrated in FIGS. 5C and 5D, the cluster may refer to a plurality of papillary muscles 502, 504 that has an outer peripheral boundary defined by the at least partially encircling band 506 and having an inner region on side of the papillary muscles 502, 504 opposite the outer peripheral boundary.

In order to loop a single band around the plurality of papillary muscles in a ventricle of a heart, the method may implement a first guidewire and/or a second guidewire. For example, as illustrated in FIGS. 2A-2C, the method may further include looping at least one guidewire 206 around a plurality of papillary muscles 202, 204 in the ventricle. The method may further include looping a first guidewire around a first papillary muscle, looping a second guidewire around a second papillary muscle, and interconnecting the first guidewire and the second guidewire. For example, as illustrated in FIGS. 3A-3C, the method may further include looping a first guidewire 306 around a first papillary muscle 302, looping a second guidewire 316 around a second papillary muscle 304, and interconnecting the first guidewire 306 and the second guidewire 316 outside of the body by a connector 314. In some embodiments of the present disclosure, the plurality of papillary muscles in the ventricle may include two and/or three papillary muscles.

In some embodiments, looping a single band around the plurality of papillary muscles may further comprise delivering a first guidewire and/or a second guidewire to the ventricle via the at least one catheter. In some embodiments, the first guidewire and/or the second guidewire may include a string, thread, wire, suture, coil, or any other thin, elongated, flexible, and/or biocompatible member. The method may comprise looping the first guidewire around a first papillary muscle and/or looping the second guidewire around a second papillary muscle. In some embodiments, looping the first guidewire and/or the second guidewire around the first and/or second papillary muscle may include using a pre-shaped catheter whose shape aids in looping around papillary muscles. For example, as illustrated in FIGS. 6A-6B, the catheter 610 may be pre-shaped to facilitate looping the guidewire 606 around the papillary muscles 602 and 604. In another embodiment, looping the guidewire around the papillary muscle may include using a steerable catheter whose shape can be modified interactively by the user to aid in looping around the papillary muscles.

According to an embodiment of the present disclosure, the method may further comprise bringing a first end of the first guidewire out of the body. That is, a first end of the first guidewire may be out of the body while a second end of the first guidewire remains inside the body. In other embodiments, both ends of the first guidewire may be brought outside of the body, while in yet other embodiments, a first end of the first guidewire may be brought out of the body while a second end of the first guidewire remains outside the body, never having entered the body. For example, as illustrated in FIGS. 3A-3C, both ends 312 of the first guidewire 306 may be brought outside of the body. Bringing the first end of the first guidewire out of the body may include pushing the second end of the first guidewire such that the first end of the first guidewire is pushed through the catheter and out of the body. In other embodiments, bringing the first end of the first guidewire out of the body may include catching the first end of the first guidewire within the ventricle of the heart by a guidewire catching technique. For example, a magnetic guidewire catching may be implemented, wherein a magnet is used to catch the first end of the first guidewire and pull the first end of the first guidewire out of the body. While the forgoing principles describe a magnetic guidewire catching mechanism, any mechanism capable of catching the first end of the guidewire and pulling the guidewire out of the body may be used. For example, a capture loop guidewire catching mechanism, a guidewire catching basket, or any combination thereof may be used to bring the first end of the first guidewire out of the body. Bringing the first end of the first guidewire out of the body may further include passing the guidewire from one portion of a catheter to another portion of the catheter such that the guidewire is captured at the second portion of the catheter. Once the guidewire is captured at the second portion of the catheter, the catheter may be pulled out of the body in order to bring the first end of the first guidewire out of the body.

According to an embodiment of the present disclosure, the method may further comprise bringing a second end of the second guidewire out of the body. That is, a second end of the second guidewire may be out of the body while the other end of the second guidewire remains inside the body. In other embodiments, both ends of the second guidewire may be brought outside of the body, while in yet other embodiments, a second end of the second guidewire may be brought out of the body while the other end of the second guidewire remains outside the body, never having entered the body. For example, as illustrated in FIGS. 3A-3C, both ends 312 of the second guidewire 316 may be brought outside of the body through a proximal end 310 of the catheter 308. Bringing the second end of the second guidewire out of the body may include pushing the first end of the second guidewire such that the second end of the second guidewire is pushed through the catheter and out of the body. In other embodiments, bringing the second end of the second guidewire out of the body may include catching the second end of the second guidewire within the ventricle of the heart by a guidewire catching technique. For example, a magnetic guidewire catching may be implemented, wherein a magnet is used to catch the second end of the second guidewire and pull the second end of the second guidewire out of the body. While the forgoing principles describe a magnetic guidewire catching mechanism, any mechanism capable of catching the second end of the guidewire and pulling the guidewire out of the body may be used. For example, a capture loop guidewire catching mechanism, a guidewire catching basket, or any combination thereof may be used to bring the second end of the second guidewire out of the body. Bringing the second end of the second guidewire out of the body may further include passing the guidewire from one portion of a catheter to another portion of the catheter such that the guidewire is captured at the second portion of the catheter. Once the guidewire is captured at the second portion of the catheter, the catheter may be pulled out of the body in order to bring the second end of the second guidewire out of the body.

According to an embodiment of the present disclosure, the method may further comprise interconnecting the first guidewire to the second guidewire. Interconnecting the first guidewire to the second guidewire may include tying the first guidewire and the second guidewire together. In other embodiments, interconnecting the first and second guidewires may include connecting the first and second guidewires together with a built-in connector, or any other type of connector used to connect a plurality of ropes, strings, wires, or cables together. In some embodiments, interconnecting the first and second guidewires may include connecting the first and second guidewires with an applied clip, clasp, or any other type of clip, clasp, or crimp ring used to connect a plurality of ropes, strings, wires, or cables together. For example, as illustrated in FIGS. 3A-3C, one end of the first guidewire 306 and one end of the second guidewire 316 may be interconnected using a flexible connector (FIG. 3A), using a rigid connector (FIG. 3B), tying a knot (FIG. 3C), or any combination thereof. In other embodiments, the ends of the first and/or second guidewires may be interconnected using any mechanism used to connect a plurality of ropes, strings, wires, or cables together.

Consistent with the embodiments of the present disclosure, the method may further comprise pulling at least one end of the first and second guidewires after interconnecting them to thereby establish a single loop around at least the first papillary muscle and the second papillary muscle. For example, as illustrated in FIGS. 4A-4C, one end 412b of the guidewire 406 may be pulled in order to establish a single loop around the first papillary muscle 402 and the second papillary muscle 404. The papillary muscles, around which the looping occurs, may include chordae or base portions of the muscles to which chordae are attached. In some embodiments, the papillary muscles, around which the looping occurs, may include multiple papillary muscle heads or multiple papillary muscle bodies. In some embodiments, the papillary muscles, around which the looping occurs, may include trabeculae of the papillary muscles. For example, looping the first and second guidewires around the papillary muscles may include passing the first and second guidewires through the plurality of spaces among the trabeculae between the papillary muscles and a wall of the ventricle.

Embodiments of the present disclosure may further include directing, using the guidewire, a band around the plurality of papillary muscles. Directing, using the guidewire, the band around the plurality of papillary muscles may include directing the band such that the band at least partially encircles between two and three papillary muscles simultaneously. In other embodiments, directing the band around the plurality of papillary muscles may include passing the band through the spaces among the trabeculae between the plurality of papillary muscles and the wall of the ventricle of the heart. In yet another embodiment, directing the band around the plurality of papillary muscles may include passing the band through the spaces among the trabeculae positioned along the walls of the ventricle of the heart. Looping a single band around a plurality of papillary muscles may be according to any of the techniques and mechanisms described above, or any combination thereof.

According to another embodiment of the present disclosure, the band may be sized to simultaneously encircle, i.e. partially or completely surround, a plurality of papillary muscles and pull the plurality of papillary muscles toward each other. For example, as seen in FIGS. 5C and 5D, the band 506 may be sized to simultaneously encircle the papillary muscles 502, 504 and pull the papillary muscles 502, 504 toward each other. While FIGS. 5C and 5D illustrate the band 506 encircling the papillary muscles 502, 504, the band 506 may also pass through a plurality of spaces among a trabeculae in the ventricle of the heart to pull the walls of the ventricle of the heart inwards by tightening the band 506. Accordingly, by pulling the walls of the ventricle of the heart inwards, the band 506 may also pull the papillary muscles 502, 504 closer to each other. Alternatively, the band may be a tube or a portion of the band may be a tube. For example, a first portion of the band may be a tube whereas a second portion of the band may not be a tube. In some embodiments of the present disclosure, the band may include at least one of polytetrafluoroethylene (PTFE), expanded polytetrafluoroethylene (ePTFE), Dacron, and/or any other biologically inert synthetic material with appropriate tensile strength for use in pulling the papillary muscles closer together. In other embodiments, the band may be manufactured by extrusion, knitting, weaving, braiding, or any other method of forming the biologically inert synthetic material into a band or a tubular band. In some embodiments the band may be elastic or non-elastic or partially elastic. In other embodiments, a part of the band may be elastic and a part of the band may be non-elastic. According to some embodiments of the present disclosure, the band may be made of more than one material. That is, a part of the band may be made of one material while another part of the band may be made of a different material. In yet another embodiment, the band may be made of biological material from the patient, from another human donor, or from animal derived material.

According to another embodiment of the present disclosure, the method of improving cardiac function may further comprise transcatheterly tightening the band to contract the outer peripheral boundary of the cluster and thereby pull the papillary muscles closer together such that the band contacts the outer peripheral boundary portions of the plurality of papillary muscles without contacting the inner region and such that the inner region is devoid of any portion of the band. For example, as illustrated in FIGS. 5C and 5D, the band 506 may contact the outer peripheral boundary portions of the plurality of papillary muscles 502, 504 and thereby pull the papillary muscles 502, 504 closer together without contacting the inner region of the papillary muscles 502, 504.

According to various exemplary embodiments of the present disclosure, transcatheterly tightening the band to contract the outer peripheral boundary and thereby pull the papillary muscles closer together may include passing a pull-string through the band, pulling the ends of the pull-string through a catheter to tighten the band, and using a transcatether suture lock to lock the pull-string into a loop of a desired and/or appropriate size. For example, as illustrated in FIG. 7, a pull-string 706 may be passed through a catheter 708 and through the band 710 to facilitate tightening of the band 710 in a single loop around the plurality of papillary muscles 702, 704. In other embodiments, tightening the band in a single loop around the plurality of papillary muscles may include passing a self-locking pull string through the band and pulling one or both ends of the pull-string to tighten the band around the plurality of papillary muscles. Pulling one or both ends of the pull-string may cause the pull-string to self-lock into a loop of the appropriate size. In another embodiment of the present disclosure, tightening the band in a single loop around the plurality of papillary muscles may include pulling a plurality of pull-strings attached to both ends of the band through a catheter. Pulling the plurality of pull-strings attached may tighten the band. Using a transcatheter suture lock, the pull-string may be locked into place, thereby forming the band into a loop of an appropriate and/or desired size.

The pull-string may be self-locking or the pull-string may be locked using another locking mechanism. In some embodiments, the pull-string may be coupled to any mechanism capable of locking the band into a looped configuration. In some embodiments of the present disclosure, a self-locking pull-string may be similar in construction to a beaded locking cable tie, in which a string includes one or more beads in fixed positions along the length of the string. As the beads pass through a locking grasper, the string and/or the band may be locked into a fixed position because the beads will not be able to pass in the opposite direction as it passes through the locking grasper. The self-locking pull-string may be locked at a position, at which the papillary muscles are pulled towards each other in order to reposition the papillary muscles.

In some embodiments, pulling the papillary muscles closer together may include pulling the papillary muscles until the opposing surfaces of each of the papillary muscles are in contact with each other. In other embodiments, pulling the plurality of papillary muscles toward each other may include pulling the papillary muscles so that the opposing surfaces of each of the papillary muscles are closer to each other than they were before. In yet another embodiment, pulling the papillary muscles toward each other may include pulling the papillary muscles until the distance between the opposing surfaces of each papillary muscle meets a certain predetermined value or range of values. For example, the papillary muscles may be pulled until the distance between the opposing surfaces of each of the papillary muscles is less than a predetermined distance or within a predetermined range of a predetermined distance. According to another embodiment of the present disclosure, pulling the papillary muscles closer together may include pulling the papillary muscles so that the outer periphery of the cluster has a predetermined circumference. The predetermined circumference may be smaller than the circumference of the outer periphery of the cluster before transcatheterly tightening the band. For example, FIG. 5A illustrates a normal heart with properly positioned papillary muscles. On the other hand, FIG. 5B illustrates a heart with dilated cardiomyopathy showing enlarged ventricle and displaced papillary muscles 502 and 504. As such, a band 506 may be looped around the papillary muscles 502 and 504 in order to pull them closer to each other, for example, as illustrated in FIG. 5C. In another example, the plurality of papillary muscles 502 and 504 may be pulled towards each other until the opposing surfaces of each of the papillary muscles 502 and 504 are in contact with each other, as illustrated in FIG. 5D. In some embodiments, the method may further comprise pulling the papillary muscles into contact with each other without any intervening material between the papillary muscles.

While the present disclosure is described herein with reference to illustrative embodiments of catheters, bands, and guidewires used for particular applications, such as for papillary muscle repositioning and improving cardiac function, it should be understood that the embodiments described herein are not limited thereto. Those having ordinary skill in the art and access to the teachings provided herein will recognize additional modifications, applications, embodiments, and substitution of equivalents that all fall within the scope of the disclosed embodiments. Accordingly, the disclosed embodiments are not to be considered as limited by the foregoing or following descriptions.

The many features and advantages of the present disclosure are apparent from the detailed specification, and thus it is intended by the appended claims to cover all such features and advantages of the present disclosure that fall within the true spirit and scope of the present disclosure. Further, since numerous modifications and variations will readily occur to those skilled in the art, it is not desired to limit the present disclosure to the exact construction and operation illustrated and described and accordingly, all suitable modifications and equivalents may be resorted to, falling within the scope of the present disclosure.

Moreover, those skilled in the art will appreciate that the conception upon which this disclosure is based may readily be used as a basis for designing other structures, methods, and systems for carrying out the several purposes of the present disclosure. Accordingly, the claims are not to be considered as limited by the foregoing description.

What is claimed is:

1. A method of improving cardiac function, the method comprising:
   delivering a band to a ventricle of a heart via at least one catheter;
   guiding the band through the heart to form a loop;
   pulling walls of the ventricle of the heart inwards by tightening the band following formation of the loop;
   following tightening, locking the band in the loop; and
   removing the at least one catheter from the heart.

2. The method of claim 1, wherein tightening the band to pull the walls of the ventricle inward causes papillary muscles to move closer together.

3. The method of claim 1, wherein the band is in a form of a tube, and wherein delivering the band includes passing the band over a guidewire.

4. The method of claim 1, wherein the band is hollow, and wherein delivering the band includes passing the band over a guidewire.

5. The method of claim 1, wherein the guidewire is steerable.

6. The method of claim 1, wherein a circumference of the loop after tightening the band is smaller than the circumference of the loop before tightening the band.

7. The method of claim 1, wherein at least a portion of the band does not include a hollow tube.

8. The method of claim 1, wherein the band is manufactured by braiding.

9. The method of claim 1, wherein delivering the band to the ventricle occurs transvenously.

10. The method of claim 1, performed in a left ventricle of the heart.

11. The method of claim 1, wherein the band is self-locking.

12. The method of claim 1, wherein tightening the band to pull the walls of the ventricle inward includes tightening the band until the loop reaches a desired size.

13. The method of claim 1, wherein locking the band in the loop is accomplished with a suture lock.

14. A method of improving cardiac function, the method comprising:
   delivering a tube to a ventricle of a heart via at least one catheter;
   guiding the tube through the heart to form a loop;
   pulling walls of the ventricle of the heart inwards by tightening the tube following formation of the loop;
   following tightening, locking the tube in a looped configuration; and
   removing the at least one catheter from the heart.

15. The method of claim 14, wherein delivering the tube to the ventricle includes delivering the tube over a guidewire.

16. The method of claim 14, wherein the tube is manufactured by braiding.

17. The method of claim 15, wherein the guidewire is steerable.

18. The method of claim 14, wherein at least a portion of the tube is not hollow.

19. The method of claim 14, wherein delivering the tube to the ventricle occurs transvenously.

20. The method of claim 14, wherein a circumference of the loop after tightening the tube is smaller than the circumference of the loop before tightening the tube.

* * * * *